United States Patent [19]

Williams et al.

[11] Patent Number: 5,217,710
[45] Date of Patent: Jun. 8, 1993

[54] STABILIZED PEROXIDE GELS CONTAINING FLUORIDE

[75] Inventors: David R. Williams, Monroe; Christine W. Ryles, Milford; Alexander G. Ziemkiewicz, Shelton, all of Conn.

[73] Assignee: Chesebrough-Pond's USA Co., Greenwich, Conn.

[21] Appl. No.: 846,315

[22] Filed: Mar. 5, 1992

[51] Int. Cl.$^5$ .................. A61K 7/16; A61K 7/18; A61K 7/20; A61K 33/40

[52] U.S. Cl. .................. 424/52; 424/49; 424/53; 424/613; 424/616; 424/673; 424/676; 424/717; 222/94; 222/192; 206/219; 206/216; 215/6

[58] Field of Search .................. 424/53, 616, 49-58, 424/673, 676

[56] References Cited

U.S. PATENT DOCUMENTS

| | | | |
|---|---|---|---|
| 2,004,809 | 6/1935 | Gilbert et al. | 23/251 |
| 2,658,818 | 11/1953 | Stanley et al. | 23/207.5 |
| 3,429,666 | 2/1969 | Morris et al. | 23/207.5 |
| 3,577,521 | 5/1971 | Scheller et al. | 424/55 |
| 4,130,501 | 12/1978 | Lutz et al. | 252/186 |
| 4,343,785 | 8/1982 | Schmolka | 424/40 |
| 4,363,794 | 12/1982 | Ochai et al. | 424/152 |
| 4,528,180 | 7/1985 | Schaeffer | 424/52 |
| 4,534,945 | 8/1985 | Hopkins et al. | 423/273 |
| 4,687,663 | 8/1987 | Schaeffer | 424/52 |
| 4,837,008 | 6/1989 | Rudy et al. | 424/53 |
| 4,849,213 | 7/1989 | Schaeffer | 424/52 |
| 4,891,211 | 1/1990 | Winston | 424/52 |
| 4,895,721 | 1/1990 | Drucker | 424/53 |
| 4,902,497 | 2/1990 | Crisanti et al. | 424/52 |
| 4,980,152 | 12/1990 | Frazier et al. | 424/52 |
| 4,980,153 | 12/1990 | Jackson et al. | 424/52 |
| 5,037,633 | 8/1991 | Ziemkiewicz et al. | 424/49 |
| 5,037,634 | 8/1991 | Williams et al. | 424/49 |
| 5,059,417 | 10/1991 | Williams et al. | 424/53 |
| 5,078,672 | 1/1992 | Dougherty et al. | 423/273 |
| 5,085,853 | 2/1992 | Williams et al. | 424/53 |
| 5,094,842 | 3/1992 | Riley | 424/52 |
| 5,096,702 | 3/1992 | Rolla et al. | 424/52 |

FOREIGN PATENT DOCUMENTS

| | | | |
|---|---|---|---|
| 376706 | 7/1990 | European Pat. Off. | 424/616 |
| 1567519 | 5/1970 | Fed. Rep. of Germany | 424/616 |
| 2343797 | 10/1977 | France | 424/616 |
| 90/11967 | 10/1990 | PCT Int'l Appl. | 424/616 |
| 2085862 | 5/1982 | United Kingdom | 424/616 |

OTHER PUBLICATIONS

Bellinger et al. Ind. Eng. Chem. 38(3): 310-320 Mar. 1946 Chemical Propellants—Corrosion & Stability Studies.

Masin et al. C.A. 105:158866h (1986)/Czech CS231929 15 Jun. 1986.

Periodontics and Oran Hygiene, Keyes, Jan. 1978, pp. 51-56.

*Primary Examiner*—Shep K. Ross
*Attorney, Agent, or Firm*—Milton L. Honig

[57] ABSTRACT

An oral composition is provided that includes a peroxygen compound such as hydrogen peroxide, a fluoride-containing anticaries agent and a tin compound, especially stannous chloride. The tin compound stabilizes the peroxygen compound against decomposition that ordinarily would be induced by the presence of fluoride.

13 Claims, No Drawings

STABILIZED PEROXIDE GELS CONTAINING FLUORIDE

BACKGROUND OF THE INVENTION

1. Field of the Invention

The invention relates to dental products for promoting health in the oral cavity.

2. The Related Art

Oral compositions containing both a peroxide and sodium bicarbonate have been acclaimed by the dental profession, especially through the work of Keyes. See Keyes et al. "Periodontics and Oral Hygiene", January 1978, pages 51-56. Formulations based on the Keyes technology, especially the peroxide component, are particularly prone to decomposition. The literature has reported considerable research directed at the stability problem. For instance, see U.S. Pat. Nos. 3,577,521 (Scheller), 4,837,008 (Rudy et al.), 4,130,501 (Lutz), 4,895,721 (Drucker) and 4,343,785 (Schmolka). A quite successful approach to the problem has involved physical segregation of the peroxide into a compartment separate from co-reactive ingredients. U.S. Pat. Nos. 4,849,213, 4,687,663 and 4,528,180, all to Schaeffer, disclose a package with a dual-compartment package respectively storing a peroxide gel and a bicarbonate paste.

From the aforementioned art, it becomes apparent that hydrogen peroxide compositions should be formulated as simply as possible to minimize potential interactions between the peroxide and the remaining ingredients.

Fluoride anion is known by those skilled in the art as a destabilizing factor in peroxide gels. The desirability of achieving anticaries protection for oral products has prompted formulators to seek a satisfactory means to allow fluoride incorporation. In U.S. Pat. Nos. 5,037,633 and 5,037,634 to Williams et al. and Ziemkiewicz et al., respectively, the problem was solved by incorporating sodium fluoride into a bicarbonate paste intended to be co-extruded with a peroxide gel, each from a separate compartment of a dual-compartment container. See also U.S. Pat. No. 5,059,417 (Williams et al.) detailing the peroxide technology.

While relegating fluoride to the bicarbonate component may solve the anticaries problem, the U.S. Food, Drug and Cosmetic Administration regulations would further necessitate use of a mechanism that dispenses a constant volume of both peroxide gel and bicarbonate paste; accurate dosage of fluoride based on total dentifrice volume is thereby ensured. Only with a special, costly pump is such precise delivery achieveable.

Consequently, a system has been sought which permits both the bicarbonate and the peroxide components to each incorporate an identical fluoride anticaries agent thereby eliminating need for a costly pump.

Beyond stabilization, any new anticaries system must have consumer satisfactory taste and have no disruptive influence upon rheology, product color or other physical parameters.

Accordingly, it is an object of the present invention to provide a peroxide-containing composition capable of use with a bicarbonate composition wherein both compositions contain a fluoride anticaries agent and there is no adverse effect upon product stability.

A further objective of the present invention is to provide a peroxide composition and a bicarbonate composition held in separate compartments of a dual-compartment delivery system wherein each of the compositions contains an identical fluoride anticaries agent.

A still further objective of the present invention is to provide a peroxide composition that incorporates a fluoride anticaries agent such that the composition has consumer-acceptable taste and maintains color, e.g. blue.

Another object of the present invention is to provide a method for inhibiting caries and also promoting gum health through application of a peroxide and a bicarbonate composition, each containing a fluoride compound and each delivered simultaneously from separate compartments of a dual-compartment dispenser.

These and other objects of the present invention will become more readily apparent upon consideration of the more detailed description and Examples which follow.

SUMMARY OF THE INVENTION

An oral composition is provided comprising:

(i) from about 0.1 to about 10% by weight of a peroxygen compound;

(ii) a physiologically-acceptable fluoride-containing compound present in an effective amount to inhibit formation of caries on teeth; and (iii) a tin compound present in an effective amount to stabilize the peroxygen compound against decomposition by the fluoride-containing compound.

A method is also provided for maintaining protection against caries formation, the method including applying to the teeth a composition comprising:

(i) from about 0.1 to about 10% by weight of a peroxygen compound;

(ii) a physiologically-acceptable fluoride-containing compound present in an effective amount to inhibit formation of caries on teeth; and (iii) a tin compound present in an effective amount to stabilize the peroxygen compound against decomposition by the fluoride-containing compound.

DETAILED DESCRIPTION

Now it has been discovered that tin compounds, especially stannous ions, have the unexpected ability to stabilize hydrogen peroxide in the presence of a fluoride compound such as sodium fluoride.

Thus, a key element of the present invention is a tin compound which may be in the form of inorganic or organic tin salts.

Among suitable inorganic salts are those of tin chloride, tin bromide, tin sulphate, tin pyrophosphate, tin bromate, tin nitrate, tin nitrite, tin carbonate, tin oxide, tin ammonium halide, and combinations thereof. For regulatory purposes, it may be desirable not to formulate the tin compound as stannous fluoride.

Illustrative of suitable organic tin compounds are tin oxalate, tin citrate, tin tartrate, tin maleate, tin ascorbate, tin lactate, tin benzoate, tin sorbate, tin acetylacetonate and combinations thereof.

The term "tin" includes both stannous and stannic oxidation states, with a special preference for stannous compounds. Amounts of the tin compound will range from about 0.005 to about 5%, preferably from about 0.01 to about 2.5%, optimally between about 0.05 and about 1.5% by weight of the peroxide composition.

Another important component of the peroxide composition is that of a fluoride anticaries compound. Illustrative of fluoride compounds are sodium fluoride, potassium fluoride, calcium fluoride, magnesium fluoride, stannous fluoride, stannous monofluorophosphate, sodium monofluorophosphate and copper fluoride. These sources should release anywhere from about 25 to 3500 ppm of fluoride ion. The anticaries agent will be present in an amount from about 0.01 to about 5%, preferably from about 0.1 to about 2.5%, optimally between about 0.2 and about 1.5% by weight of the peroxide composition.

A variety of peroxygen compounds may be employed including urea peroxide, hydrogen peroxide and the salts of perborate, persilicate, perphosphate and percarbonate. The most suitable for this invention is hydrogen peroxide. The amount of the peroxygen compound may range from about 0.1 to about 10% by weight. In terms of active weight hydrogen peroxide, the amount will range from about 0.5 to about 5%, preferably from about 0.8 to about 4%, optimally between about 1 and 3% by weight.

Oral compositions of the present invention may be in the form of either a toothpaste, a gel, a tablet, a powder or a mouthwash. The preferred embodiment of the present invention is a hydrogen peroxide gel composition in either mouthwash or gel form in combination with a bicarbonate-containing composition.

Water may be present in the compositions in amounts ranging from about 20 to about 95% by weight. When the peroxide composition is a gel, the amount of water may range from about 30 to about 55%, optimally between about 35 and 45% by weight.

Structurants are necessary where the peroxide composition is in the form of a gel. Most suitable as the structurant are the polyoxyethylene-polyoxypropylene copolymers where the hydrophobic portion, represented by ($C_3H_6O$), has a molecular weight ranging from about 2,750 to 4,000 and the hydrophilic portion, represented by ($C_2H_4O$), constitutes about 70 to 80% of the weight of the copolymer. Commercially the copolymers are available from the BASF Corporation under the trademark, Pluronic F88, F99, F108 and F127. Most preferred is Pluronic F127 (hereinafter referred to by its CTFA name, Poloxamer 407) which has a molecular weight ranging from about 10,000 to 15,000, and containing about 70% of the hydrophilic polyoxyethylene moiety. Amounts of the copolymer can range anywhere from 18 to 25% by weight, preferably between 19 and 24%. Poloxamers are particularly suitable for this invention because of their wide pH tolerance, good compatibility with hydrogen peroxide and unique gel properties.

Glycerol is another preferred ingredient of the peroxide composition when in gel or rinse form. Amounts of glycerol may range from about 5 to about 50%, preferably between about 5 to about 20% by weight for the rinse but preferably between about 35 and 45% by weight for the gel.

Adjunct minor ingredients may also be present in the composition of this invention. Included may be small amounts of colorant, flavor and antioxidant.

Oral compositions of the present invention may include, besides a peroxide composition, an additional separate bicarbonate-containing composition, each held within a separate container available for simultaneous delivery in substantially equal volumes for use in the mouth.

The bicarbonate composition will also contain a fluoride anticaries compound selected from the same fluoride compounds in essentially identical amounts to those described hereinabove with respect to the peroxide composition. Especially preferred is sodium fluoride. Bicarbonate salts will be present in alkali metal form, examples of which are sodium and potassium. Typically, the concentration of bicarbonate salt will range from about 0.5 to about 80%, preferably from about 5 to about 50%, optimally between about 8 and about 20% by weight of the total combined dental product. The pH of the bicarbonate composition may range from about 7.0 to about 9.5, most preferably about 8.0 to 9.0. When the bicarbonate composition is in toothpaste or gel form, there will typically be included a natural or synthetic thickening agent in an amount from about 0.1 to 10%, preferably about 0.5 to 5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Surfactants are normally also included in the bicarbonate compositions. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to about 5% by weight.

When in the form of a toothpaste or gel, the bicarbonate compositions will normally include an abrasive in addition to the bicarbonate. Abrasives may be selected from water-insoluble alkali or alkaline earth metal salts of metaphosphate (IMP), calcium carbonate, aluminate and silicate. Especially preferred are silica, dicalcium phosphate and calcium carbonate. Amounts of the abrasive will range form about 5 to about 80% by weight.

Tartar control agents may be incorporated into compositions of this invention. Especially effective will be agents containing phosphorous. Inorganic phosphorous tartar control agents may include sodium tripolyphosphate or any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tartar control agents include polyphosphonates such as disodium ethane-1-hydroxy-1,1-diphosphonate (EHDP), methanediphosphonic acid, and 2-phosphonobutane-1,2,4-tricarboxylic acid.

Flavors are usually present in both the peroxide and, when suitable, bicarbonate compositions. These flavors may be based on oils of spearmint and peppermint. Examples of other flavoring materials include menthol, clove, wintergreen, eucalyptus and aniseed. Flavors may range in concentration from about 0.1 to about 5% by weight of the total composition.

Sweetening agents such as saccharin, sodium cyclamate, aspartame, sucrose and the like may be included at levels from about 0.1 to about 5% by weight of the total composition.

Other additives may also be incorporated into the oral compositions including preservatives, silicones, other synthetic or natural polymers such as Gantrez S-97 ®, and anti-gingivitis actives.

The following examples will more fully illustrate the embodiments of this invention. All parts, percentages and proportions referred to herein and in the appended claims are by weight of the total composition unless otherwise stated.

EXAMPLE 1

Typical of the present invention is a peroxide gel composition whose formulation is detailed under Table I. The formulation of Table I may be utilized in combination with a bicarbonate composition detailed under Table II, each of the compositions being held in a separate compartment of a dual-compartment dispenser.

TABLE I

Peroxide Gel Component

| Ingredient | Wt. % |
| --- | --- |
| Pluronic F127 | 20.000 |
| Glycerin | 40.000 |
| Hydrogen Peroxide (35% food grade) | 4.285 |
| Methyl Salicylate | 0.500 |
| Sodium Fluoride | 0.230 |
| Stannous Chloride | 0.230 |
| FD&C Blue 1 | 0.005 |
| Phosphoric Acid (85% w/w) | 0.150 |
| Deionized water | Balance |

TABLE II

Bicarbonate Paste Component

| Ingredient | Wt. % |
| --- | --- |
| Polyol II (sorbitol and other sugars) | 48.710 |
| Syloid 63XX (abrasive silica) | 15.000 |
| Sodium Bicarbonate | 10.000 |
| PEG 32 (polyethylene glycol) | 5.000 |
| Sylox 15x (thickening silica) | 4.600 |
| Sodium Lauryl Sulfate | 2.980 |
| SD Alcohol 38B | 2.850 |
| Cellulose Gum | 0.800 |
| Menthol | 0.500 |
| Sodium Saccharin | 0.500 |
| Sodium Fluoride | 0.230 |
| Titanium Dioxide | 0.300 |
| Deionized water | Balance |

EXAMPLE 2

A series of stability experiments were conducted to evaluate the effect of stannous chloride and concentration thereof on a peroxide gel composition.

The test employed was the Peroxide Stability/Stress Test (PSST). Samples were exposed to accelerated aging at a temperature of 95° C. over a 6-hour period. These aging conditions were found to have good correlation with 3-month storage stability testing at 105° F. Peroxide content of the gel was assayed by oxidizing potassium iodide to iodine and titrating with sodium thiosulphate on an auto-titrator fitted with a redox electrode.

In addition to determining the remaining peroxide after the 6-hour heating period, the color of the gel was also recorded as an indication of long-term stability.

Gel compositions having the same ingredients (except for different fluoride and stannous components) as that identified under Table I of Example 1 were herein evaluated. Table III outlines the results of these tests.

TABLE III

Peroxide Stability Results

| Fluoride Compound | Tin Compound | % Recovered Peroxide |
| --- | --- | --- |
| Sodium monofluorophosphate | None | 0.0 |
| Sodium fluoride | None | 0.0 |
| None | None | 81.3 |
| None | Stannous chloride | 47.5 |
| Sodium fluoride | Stannous chloride | 96.0 |

Evident from Table III is that stannous chloride enables the sodium fluoride gel composition to maintain intact essentially all the hydrogen peroxide component even under the stringent conditions of the PSST Evaluation. Indeed, the gel with sodium fluoride and stannous chloride is even more stable than the control gel without any of the aforementioned two components. Stannous chloride by itself does nothing to stabilize, and in fact, destabilizes, the peroxide gel composition.

TABLE IV

| Stannous Chloride Concentration (%) | % Recovery Hydrogen Peroxide |
| --- | --- |
| 0 | 0 |
| 0.035 | 9.5 |
| 0.07 | 30.3 |
| 0.14 | 96.1 |
| 0.27 | 98.7 |
| 0.54 | 96.3 |
| 1.08 | 64.6 |
| 2.16 | 6.2 |

Table IV provides results which indicate that stannous chloride has an optimum efficacy between 0.1 and 1.0% by weight of the hydrogen peroxide gel composition (Table I formula) under a constant sodium fluoride level.

EXAMPLE 3

This Example illustrates the effect of pH upon the peroxide gel stability at constant stannous and fluoride levels. The peroxide composition outlined under Table I was employed for these tests. Acidity was changed by manipulating the amount of phosphoric acid present.

TABLE V

Effect of pH on Peroxide Gel Stability (Sn Present)

| pH | % Recovery Hydrogen Peroxide |
| --- | --- |
| 2.0 | 89 |
| 2.5 | 97 |
| 3.0 | 98 |
| 3.5 | 100 |

The test was conducted at a constant fluoride concentration of 1150 ppm and a total stannous chloride dihydrate level of 0.27%. Based on the PSST Evaluation, the stability improved as pH rose from 2.0 up to 3.5. This contrasts significantly with the decrease in the PSST found above pH 3.0 for a peroxide gel which did not include a stannous salt. See Table VI.

TABLE VI

Effect of pH on Peroxide Gel Stability (Sn Absent)

| pH | % Recovery Hydrogen Peroxide |
| --- | --- |
| 2.0 | 97 |
| 2.5 | 94 |
| 3.0 | 90 |
| 3.5 | 46 |
| 4.4 | 0 |

The foregoing description and Examples illustrate selected embodiments of the present invention. In light thereof, various modifications will be suggested to one skilled in the art, all of which are within the spirit and purview of this invention.

What is claimed is:

1. A dental product for maintaining protection against caries formation which is a dual-compartment dispenser comprising:
   (A) a first compartment of the dual-compartment disperser containing a first composition comprising:
      (i) from about 0.1 to about 10% by weight of a peroxygen compound that provides hydrogen peroxide;
      (ii) a physiologically-acceptable fluoride-containing compound present in an effective amount to inhibit formation of caries on teeth; and
      (iii) a tin compound other than stannous fluoride present in an effective amount to stabilize the peroxygen compound against decomposition by the fluoride-containing compound; and
   (B) a second compartment of the dual-compartment dispenser containing a second composition comprising:
      (i) from about 0.1 to about 30% by weight of an alkali metal bicarbonate; and
      (ii) a fluoride anticaries compound in an amount essentially identical to the amount in the first composition.

2. A dental product according to claim 10 wherein the fluoride anticaries agent is sodium fluoride.

3. A dental product according to claim 2 wherein the sodium fluoride is present in a concentration from about 0.1 to about 5% by weight in each of the first and second compartments.

4. A composition according to claim 10 wherein the tin compound is stannous chloride.

5. A dental product according to claim 4 wherein the stannous chloride is present in an amount from about 0.005 to about 5% by weight.

6. A dental product according to claim 1 further comprising a blue colorant in the first compartment which is FD&C Blue 1 present in an effective amount to color the first composition.

7. A dental product according to claim 1 wherein the pH in the first composition ranges from 3.0 to 5.0.

8. A dental product according to claim 1 wherein the peroxygen compound is selected from the group consisting of urea peroxide, hydrogen peroxide and the salts of perborate, persilicate, perphosphate and percarbonate.

9. A dental product according to claim 8 wherein the peroxygen compound is hydrogen peroxide.

10. A dental product according to claim 9 wherein the peroxygen compound is present in an amount from about 0.5 to 3% by weight.

11. A dental product according to claim 3 wherein the sodium fluoride is present in a concentration from about 0.1 to about 0.8% by weight in each of the first and second compartments.

12. A dental product according to claim 1 wherein the fluoride-containing compound is selected from the group consisting of sodium fluoride and sodium monofluorophosphate.

13. A method for maintaining protection against caries formation, the method including dispensing simultaneously and in substantially equal volumes from a dental product, which is a dual-compartment dispenser, a first and second composition held in separate compartments of the dispenser and applying same to teeth, wherein:
   (A) the first composition comprises:
      (i) from about 0.1 to about 10% by weight of a peroxygen compound that provides hydrogen peroxide;
      (ii) a physiologically-acceptable fluoride-containing compound present in an effective amount to inhibit formation of caries on teeth; and
      (iii) a tin compound other than stannous fluoride present in an effective amount to stabilize the peroxygen compound against decomposition by the fluoride-containing compound; and
   (B) the second composition comprising:
      (i) from about 0.1 to about 30% by weight of an alkali metal bicarbonate; and
      (ii) a fluoride anticaries compound in an amount essentially identical to the amount in the first composition.

* * * * *